(12) United States Patent
Sayag et al.

(10) Patent No.: US 9,110,309 B2
(45) Date of Patent: Aug. 18, 2015

(54) METHOD FOR SELECTING PROGRESSIVE OPHTHALMIC LENSES

(75) Inventors: Jean-Philippe Sayag, Paris (FR); Benoit Grillon, Paris (FR)

(73) Assignee: ACEP FRANCE (FR)

( * ) Notice: Subject to any disclaimer, the term of this patent is extended or adjusted under 35 U.S.C. 154(b) by 27 days.

(21) Appl. No.: 13/824,184

(22) PCT Filed: Sep. 23, 2011

(86) PCT No.: PCT/FR2011/052215
§ 371 (c)(1),
(2), (4) Date: May 9, 2013

(87) PCT Pub. No.: WO2012/038676
PCT Pub. Date: Mar. 29, 2012

(65) Prior Publication Data
US 2013/0215379 A1    Aug. 22, 2013

(30) Foreign Application Priority Data
Sep. 23, 2010  (FR) .................................... 10 57684

(51) Int. Cl.
*G02C 7/06* (2006.01)
*A61B 3/113* (2006.01)
*A61B 3/14* (2006.01)
*G02C 13/00* (2006.01)

(52) U.S. Cl.
CPC ................. *G02C 7/061* (2013.01); *A61B 3/113* (2013.01); *A61B 3/14* (2013.01); *G02C 13/003* (2013.01)

(58) Field of Classification Search
CPC ..... G02C 13/003; G02C 13/005; G02C 7/061

USPC ................... 351/159.73, 159.75, 159.76, 178
See application file for complete search history.

(56) References Cited

U.S. PATENT DOCUMENTS 6,257,721 B1 *    7/2001    Hayashi et al. ................ 351/204
2013/0057825 A1 *    3/2013    Kato ........................ 351/159.42

FOREIGN PATENT DOCUMENTS

| EP | 1 038 495 A2 | 9/2000 |
| FR | 2 896 682 A1 | 8/2007 |
| FR | 2 898 193 A1 | 9/2007 |
| FR | 2 931 002 A1 | 11/2009 |

OTHER PUBLICATIONS

International Search Report and Written Opinion dated Feb. 10, 2012 issued in corresponding International patent application No. PCT/FR2011/052215.

* cited by examiner

*Primary Examiner* — Darryl J Collins
(74) *Attorney, Agent, or Firm* — Ostrolenk Faber LLP

(57) ABSTRACT

The disclosure relates to a method for selecting progressive ophthalmic lenses for a given frame and wearer, the progressive ophthalmic lenses having one area for distance vision and one area for near vision, said given frame having two recesses suitable for receiving a progressive ophthalmic lens, respectively, said two recesses defining a recess midplane. The method includes the following steps: a) fitting said wearer with said given frame; b) determining the position of a first point of intersection between a first direction of the gaze of said wearer in a distance vision posture and said recess midplane; c) determining the position of a second point of intersection between the gaze of said wearer in a near vision posture and said recess midplane; d) assessing the distance between said intersection points; and, e) selecting progressive ophthalmic lenses in which the progression length corresponds to said distance assessed between said intersection points.

4 Claims, 3 Drawing Sheets

METHOD FOR SELECTING PROGRESSIVE OPHTHALMIC LENSES

CROSS-REFERENCE TO RELATED APPLICATIONS

The present application is a 35 U.S.C. §371 National Phase conversion of PCT/FR2011/052215, filed Sep. 23, 2011, which claims benefit of French Application No. 1057684, filed Sep. 23, 2010, the disclosures of which are incorporated herein by reference. The PCT International Application was published in the French language.

BACKGROUND OF THE INVENTION

1. Technical Field

The present invention pertains to a method for selecting progressive ophthalmic lenses for a given frame fitted to a determined wearer.

2. Related Art

Progressive ophthalmic lenses are associated with a medical prescription and they are housed in a frame that the wearer chooses as a function of his tastes.

Lenses of this type exhibit a far vision zone, situated in the upper part of the lens and a near vision zone situated in the lower part. These vision zones exhibit different optical characteristics. Hence, and this is a particular feature of this type of ophthalmic lens, it exhibits a progression corridor which extends from one zone to the other, and whose optical characteristics vary in a continuous manner. Thus, from the far vision zone to the near vision zone, the optical characteristics of the far vision zone evolve progressively to the optical characteristics of the near vision zone. This allows the wearer to pass from one zone to the other without inconvenience and with a certain comfort.

However, this progression corridor and especially its length may vary from one frame to another. It is indeed understood that the progression length varies as a function of the position of the ophthalmic lenses with respect to the eye, and consequently with respect to the chosen frame.

Hence, it has been contemplated to take into account the size and the shape of the frame for the purposes of optimizing the progressive ophthalmic lens is brought to an optimal level of comfort for the wearer. It will be possible especially to refer to the document FR 2 898 193, which describes a procedure for determining a progressive ophthalmic lens suited to the wearer and to the chosen frame.

The procedure calls upon representative parameters obtained on the basis of mean values which are themselves calculated on the basis of a given population sample. Despite these precautions, it turns out that certain people experience difficulties in enduring their progressive ophthalmic lenses.

Hence, a problem which arises and which the present invention is intended to solve is to provide a method for selecting progressive ophthalmic lenses as a function of the characteristics of the wearer and of the frame that he chooses, so as to yet further increase his comfort of vision.

SUMMARY OF THE INVENTION

With this aim, the present invention proposes a method for selecting progressive ophthalmic lenses for a given frame and a given wearer, the progressive ophthalmic lenses exhibiting a far vision zone and a near vision zone spaced apart by a progression length, said given frame exhibiting two recesses able respectively to receive a progressive ophthalmic lens, said two recesses defining a recess mid-plane. According to the invention the method comprises the following steps: a) said given wearer is fitted with said given frame; b) the position of a first point of intersection of a first direction of gaze of said wearer in a far vision posture and of said recess mid-plane is determined with respect to said frame; the position of a second point of intersection of a second direction of gaze of said wearer in a near vision posture and of said recess mid-plane is determined with respect to said frame; the distance which extends between said points of intersection is evaluated; and, progressive ophthalmic lenses whose progression length corresponds to said evaluated distance between said points of intersection are selected.

Thus, a characteristic of the invention resides in the customized measurement of the relative positions of the points of intersection of the recess mid-plane, respectively with the directions of gaze of the wearer in far vision and in near vision and in the evaluation of the distance which separates these points of intersection so as to select corresponding progressive ophthalmic lenses. In practice, it is for example possible to tag respectively these points of intersection with respect to the lower edge of the frame and to measure vertically the distance which separates them therefrom. It turns out that the distance which separates these points of intersection differs from one patient to another and from one frame to another and does so in relatively significant proportions. Now, progressive ophthalmic lenses are offered with standard progression lengths which are not necessarily suited in all circumstances for a given wearer fitted with a given frame. By virtue of the method according to the invention, it is possible to choose for a given wearer who has chosen a frame the progressive ophthalmic lenses whose progression length is identical to the distance which separates the points of intersection aforementioned. Additionally, if however no progressive ophthalmic lenses corresponded to this distance, the choice of the frame could be reassessed so as to identify an appropriate frame.

The direction of gaze of the wearer in a far vision posture corresponds to the direction of gaze when he is standing and observing the horizon. In a near vision posture, the direction of gaze is that of the wearer when he is reading in a natural position, for example a book that he is holding in his hands.

According to one particularly advantageous mode of implementation of the invention, said frame is equipped with a calibrated rig exhibiting three tag points spaced apart respectively by a determined distance. As will be explained hereinafter in greater detail, the calibrated rig makes it possible to measure the distance of certain characteristics of the frame in relation to certain other anthropometric characteristics of the wearer. The calculation of certain of these distances by triangulation will also be explained. It will be observed that the calibrated rig makes it possible to avoid putting tags in place on the frame itself. However, it is also possible to use the calibrated rig to measure certain of these distances and also the value of the frame height for example to measure certain other distances. Preferably, the calibrated rig sits in the upper part of the frame and it exhibits two lateral tag points neighboring the arms of the frame and joined by a bridge, as well as a central tag point situated at the end of a rod mounted perpendicularly to the bridge between the two lateral tag points.

According to a particularly advantageous characteristic, in the aforementioned step b), a first image of said frame equipped with said calibrated rig and the pupils of the eyes of said wearer is recorded along a direction neighboring said first direction of gaze, so as to determine the position of said first point of intersection with respect to said frame. As will be explained hereinafter, by virtue of the first image and according to an implementation variant, the distance which separates the lower edge of the frame and the corneal reflection of the wearer is measured, as are the relative distances of the aforementioned three tag points so as to determine the angle of the recess mid-plane with respect to a vertical plane. The angle of the mid-plane with respect to the vertical is called the pantoscopic angle. By virtue of these elements, the position of the first point of intersection between the recess mid-plane and the progressive ophthalmic lenses is determined with respect to the lower edge of the frame.

Advantageously, a first camera is provided and in that said first camera is adjusted remotely from said wearer fitted with said frame equipped with said calibrated rig and along a direction neighboring said first direction of gaze so as to record said first image. The first camera is for example adjusted to about 2 m from the wearer in a standing position and at the height of his eyes. In this way, the image obtained by the first camera can be processed and analyzed, doing so in an automatic or else semi-automatic manner, so as to obtain the aforementioned values.

Furthermore, in step c), a second image of said frame equipped with said calibrated rig and the pupils of the eyes of said wearer is recorded along a direction neighboring said second direction of gaze, so as to determine the position of said second point of intersection with respect to said frame. Measurements and a calculation comparable with that of the aforementioned step b) can be implemented to determine the position of the second point of intersection, for example with respect to the lower edge of the frame.

Hence, to do this, a mobile support bearing inscriptions and a second camera secured to said mobile support and installed through said inscriptions are provided, and said wearer fitted with said frame equipped with said calibrated rig is permitted to adjust said mobile support to a natural reading distance, so as to record said second image. Thus, by virtue of the second camera carried on the support bearing the inscriptions, it will be possible to obtain an image of the frame equipped with the rig and the pupil of the wearer's eyes from the support and along a direction neighboring the second direction of gaze of the wearer. In the same manner, as for the first camera, the image obtained can be processed and analyzed to obtain the position of the second point of intersection with respect to the lower edge of the frame.

It will be observed that these measurements and its calculations are simplified when the optical axis of the camera coincides with the direction of gaze of the wearer. If it may be considered that this is the case for the first direction of gaze in the far vision first posture, the same does not hold in the case of the second direction of gaze in the near vision posture.

According to another subject, the present invention relates to an automatic processing assembly making it possible to select progressive ophthalmic lenses for a given frame fitted on given wearer, the progressive ophthalmic lenses exhibiting a far vision zone and a near vision zone spaced apart by a progression length, said given frame exhibiting two recesses able respectively to receive a progressive ophthalmic lens, said two recesses defining a recess mid-plane. It comprises: first determination means for determining with respect to said frame, the position of a first point of intersection of a first direction of gaze of said wearer in a far vision posture with said recess mid-plane; second determination means for determining with respect to said frame, the position of a second point of intersection of a second direction of gaze of said wearer in a near vision posture with said recess mid-plane; evaluation means for evaluating the distance which extends between said points of intersection; and, selection means for selecting progressive ophthalmic lenses whose progression length corresponds to said evaluated distance between said points of intersection.

Furthermore, said first and second determination means advantageously comprise a calibrated rig intended to equip said frame, and exhibiting three tag points spaced apart respectively by a determined distance. This calibrated rig makes it possible especially, as will be explained in greater detail hereinafter, to determine by triangulation the orientation of the frames but also, the distances at the level of the wearer's eyes.

Moreover, and according to one particularly advantageous mode of implementation of the invention, said second determination means comprise a portable display screen and a camera installed on said portable display screen. The portable display screen for example a "tablet PC", surmounted by an onboard camera. Thus, and as will be explained hereinafter in greater detail, the wearer can himself adjust the display screen to the natural near vision distance and also, orient the optical axis of the camera.

Furthermore, said second determination means advantageously comprise recording and calculation means, for recording the images provided by said camera and for calculating said position of the second point of intersection of the second direction of gaze of said wearer in a near vision posture with said recess mid-plane.

Other particular features and advantages of the invention will emerge on reading the description given hereinafter of a particular embodiment of the invention, given by way of nonlimiting indication, with reference to the appended drawings in which:

DESCRIPTION OF PREFERRED EMBODIMENTS

Figure 1:
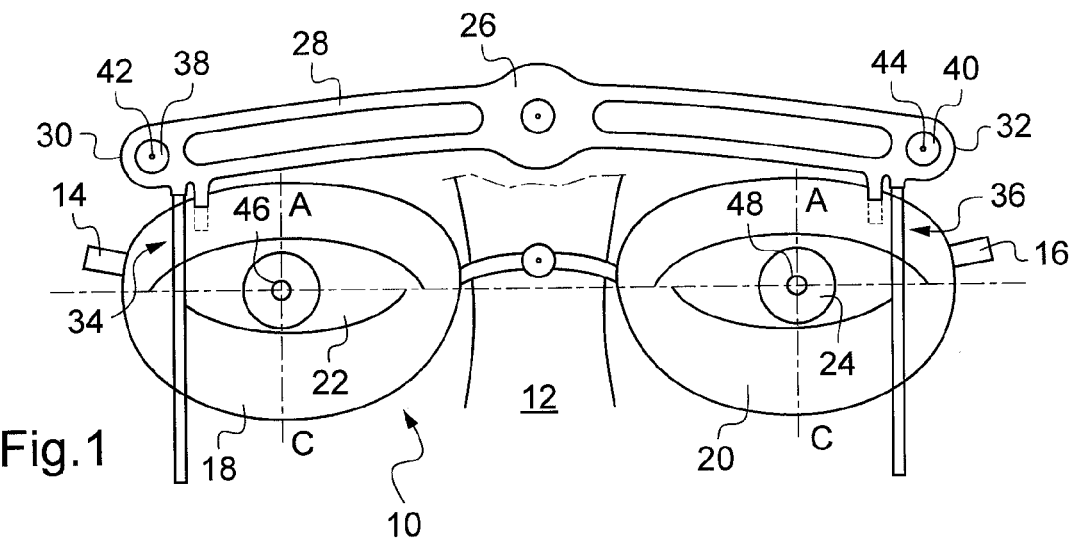
FIG. 1 is a schematic front view of the eyes of a wearer of a frame equipped with a calibrated rig.

FIG. 1 illustrates 1 illustrates a frame 10 installed on the face 12 of a wearer. This frame 10 exhibits two arms 14, 16 and two recesses 18, 20 delimited by a substantially ovoid closed structure and which extend respectively in front of the wearer's eyes 22, 24 so as to receive progressive ophthalmic lenses. Furthermore, the frame 10 is equipped with a calibrated rig 26. This calibrated rig 26 exhibits a bridge 28 which extends longitudinally and two opposite ends 30, 32 which respectively comprise a fixing bracket 34, 36. Thus, the fixing brackets 34, 36 overlap the frame 10 in the neighborhood of the latter's two respective arms 14, 16, leaving the wearer's visual space free. The calibrated rig 26 which is thus totally secured to the frame 10, exhibits two opposite tags 38, 40 installed respectively at the two opposite ends 30, 32. These two opposite tags 38, 40 exhibit respectively a white colored mark in the form of a disk, the center of which bears a black point 42, 44. Furthermore, the two black points 42, 44 are spaced a known distance apart, for example equal to exactly 110 mm.

Moreover, in this figure will be observed the pupils 46, 48 of the wearer's eyes 22, 24, which are able to exhibit at their center a white mark corresponding to the reflection of the vertex of the cornea. Thus, there appears in a front view at one and the same time the calibrated rig 26 and the two black points 42, 44 spaced a determined distance apart and in an extremely close neighboring vertical plane, the pupil 46, 48 of the wearer's eyes 22, 24.

Furthermore, the frame 10 exhibits a height AC corresponding to the maximum height of the closed structure according to a substantially vertical plane cutting the pupils 46, 48. The points A and C correspond respectively to the upper and lower edges of the frame, and their distance is perfectly determined.

Figure 2:
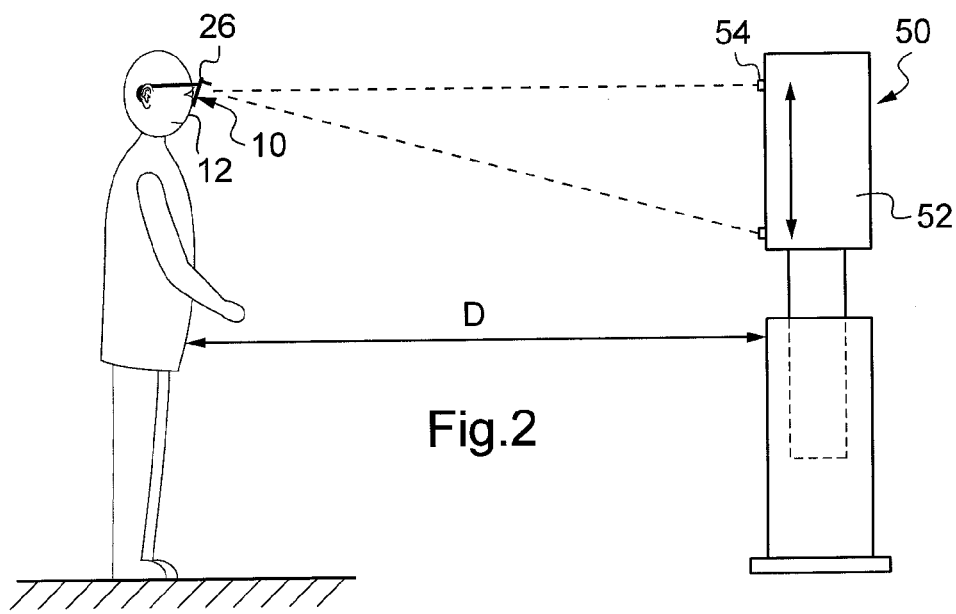
FIG. 2 is a schematic side view showing the equipped-frame wearer in a far vision posture.

In order to implement the method according to the invention, there is also provided a first installation 50 comprising a recording device 52 represented in FIG. 2. The recording device comprises at least one digital camera 54 of CCD type oriented toward the face 12 of the wearer at a distance D from the latter, equivalent to 2 m. This first installation also comprises processing means, not represented. They include an image processing module making it possible to evaluate on the basis of the images provided and recorded by the camera 54, especially the relative position of the lower and upper edges of the frame and of the corneal reflection of the pupils 46, 48. They also include a calculation module making it possible to evaluate the inclination of the mid-plane of the recesses 18, 20 with respect to the vertical. Advantageously, a lamp is installed at the level of the camera, so as obtain a very sharp corneal reflection.

The wearer is equipped with the frame 10 which is furnished with its calibrated rig 26. Here, the wearer's posture corresponds to far vision.

Figure 3:
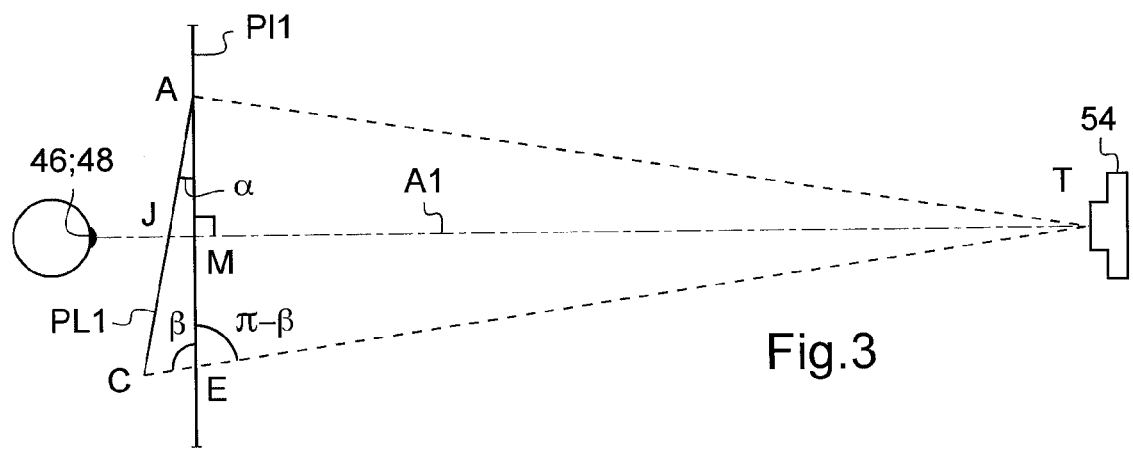
FIG. 3 is a schematic detail view of FIG. 2.

In this position, an image of the wearer's face 12 is recorded with the aid of the digital camera 54. Attention will now be turned to FIG. 3 showing the various parameters reproduced in the plane of the image Pl1. Thus, the optical axis A1 of the digital camera 54 substantially cuts the segment which joins the corneal reflection of the two pupils 46, 48 and equidistantly from these pupils 46, 48. Hence, the optical axis A1 of the digital camera 54 is perpendicular to the image plane Pl1. Found in this image plane are the upper edge A of the frame 10, the projection E of the lower edge C, as well as the projection M of the first point of intersection J of the first direction X1 of gaze of the wearer with the recess mid-plane PL defined by the recesses 18, 20 of the frame 10. It will be observed that the first direction X1 of gaze of the wearer coincides with the optical axis A1 of the digital camera 54.

It is desired in this position to ascertain the distance between the first point of intersection J and the lower edge C of the frame.

The angle $\beta$ is firstly determined. The distance TM which separates the digital camera 54 from the projected point M is known. This projected point M is situated equidistantly from the upper and lower edges of the image plane Pl1. On the one hand the pixels which separate the point M and the point E and on the other hand the pixels which separate the two black points 42, 44 of the calibrated rig 26 are enumerated on the image plane. Knowing the real distance which separates these two black points 42, 44, the real distance ME is deduced therefrom, by applying a rule of three. Thus the angle $\beta$ is derived from the triangle AEC, since $\tan(\pi-\beta)=TM/ME$.

Hence, from this is deduced the pantoscopic angle $\alpha$ between the image plane Pl1 and the recess mid-plane PL since in triangle AEC, $\alpha=\pi-\beta-\arcsin[(AE\sin\beta)/AC]$. Taking account of the previous calculation, $\alpha=\arctan[TM/ME]-\arcsin[(AE\sin\beta)/AC]$. Furthermore, the length AE is determined as hereinabove, by enumerating the pixels between the point M and the point E of the image plane Pl1 and by applying a rule of three.

The position of the point of intersection J is thus determined by calculating on the one hand the distance AM included in the image plane Pl1 by enumerating the pixels between the point A and the point M and by applying a rule of three and by dividing this distance by $\cos\alpha$ in order to obtain the distance AJ and on the other hand by subtracting the distance AJ from the known distance CA which extends between the two edges, upper and lower, of the frame 10. The value of the distance CJ is thus obtained.

Moreover, still in this far vision posture such as represented in FIG. 2, the length which extends between the corneal reflections of the two pupils 46, 48 is also measured, by enumerating the pixels which extend between the two reflections projected in the image plane Pl1 and by applying a rule of three as indicated hereinabove to determine the real distance.

The mode of determination of the position of the point of intersection of the direction of gaze of the wearer with the recess mid-plane in a near vision posture will now be described with reference to FIGS. 4 and 5.

Figure 4:
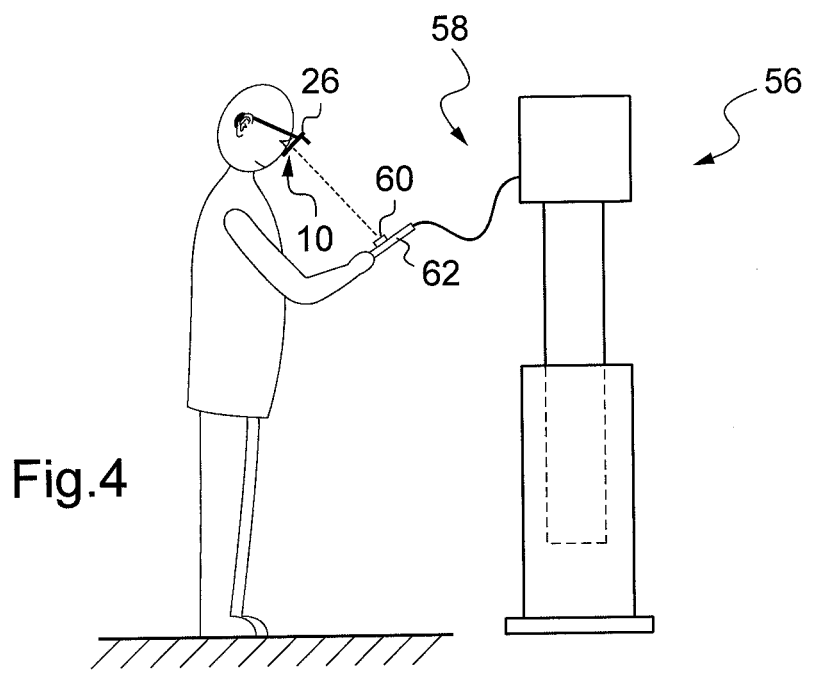
FIG. 4 is a schematic side view showing the equipped-frame wearer in a near vision posture.

Represented in FIG. 4 is the wearer equipped with the frame 10 which is furnished with its calibrated rig 26. According to the method, a second installation 56 is furthermore provided, comprising a second recording device 58 comprising a mobile digital camera 60 of CCD type. This mobile camera 60 is mounted through a support 62 on which inscriptions are featured. Hence, the wearer of the frame 10 is requested to place himself in a natural position for reading the inscriptions of the support. This relative position of the support and of the wearer's face 12 corresponds to a near vision posture. The optical axis of the camera is then oriented toward the face 12 of the wearer at a calculable distance and along a direction which does not necessarily coincide with the wearer's direction of gaze.

This second installation 56 also comprises processing means, not represented, and they include an image processing module analogous to the previous making it possible to evaluate on the basis of the images provided and recorded by the mobile digital camera 60, the distance of the latter with respect to the frame 10, the relative position of the lower and upper edges of the frame and of the corneal reflection of the pupils 46, 48. Just like the previous processing means, they include a calculation module making it possible to evaluate the inclination of the mid-plane of the recesses 18, 20 with respect to the vertical.

In this near vision posture, an image of the wearer's face 12 is recorded with the aid of the mobile digital camera 60. Attention will now be turned to FIG. 5 showing the various parameters reproduced in the plane of the image Pl2.

The optical axis A2 of the mobile digital camera 60 no longer cuts the segment which joins the corneal reflection of the two pupils 46, 48 but it extends between this segment and a segment formed by the two upper edges A of the recesses of the frame.

Figure 5:
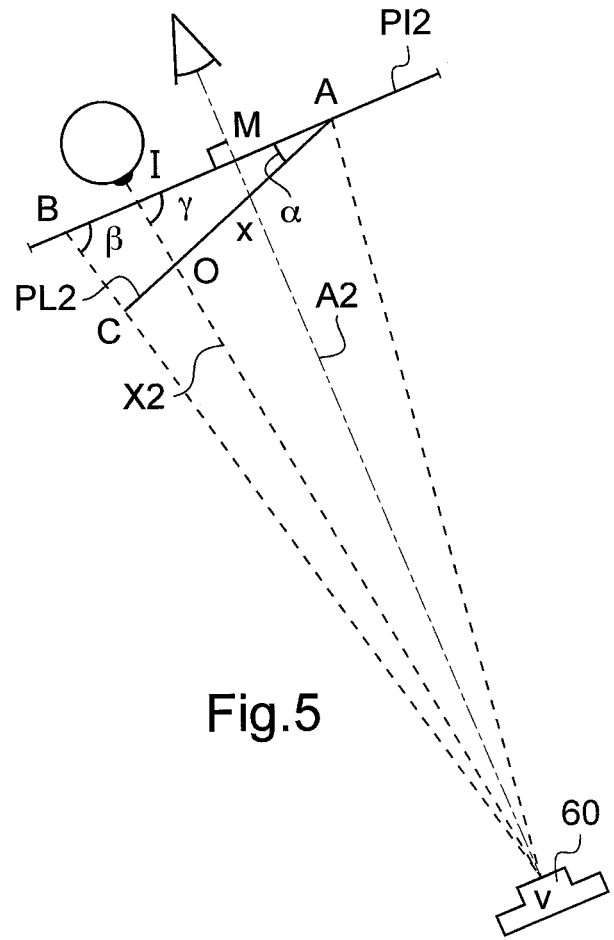
FIG. 5 is a schematic detail view of FIG. 4.

On the other hand, the optical axis A2 of the mobile digital camera 60 is by nature always perpendicular to the image plane Pl2 which in FIG. 5 is tangent to the upper edge A of the recesses of the frame.

Thus, found in this image plane Pl2 are the upper edge A of the frame 10, the projection B of the lower edge C, the intersection M of the optical axis A2 and of the image plane Pl2, as well as the projection I of the second point of intersection O of the second direction X2 of gaze of the wearer with the second recess mid-plane PL2 defined by the recesses 18, 20 of the frame 10.

It is desired in this position, as in the far vision posture, to ascertain the distance between the second point of intersection O and the lower edge C of the frame.

To do this, the distance MV which extends between the mobile digital camera 60 and the point M is firstly determined. This distance is easily determined since it corresponds to a number of pixels between the two black points 42, 44 of the calibrated rig 26.

Thereafter, the angle β is determined. The distance MV which separates the mobile digital camera 60 from the point M is therefore known. On the one hand the pixels which separate the point M and the point B and on the other hand the pixels which separate the two black points 42, 44 of the calibrated rig 26 are enumerated on the image plane Pl2. The real distance MB is deduced therefrom, by applying a rule of three. Thus from this is deduced the angle β of the triangle ABC, since $\tan \beta = MV/MB$.

Hence, from this is deduced the angle α between the image plane Pl2 and the recess mid-plane PL2 since in triangle ABC, $\alpha = \pi - \beta - \arcsin[(AB \sin \beta)/AC]$. Furthermore, the length AI is determined as hereinabove, by enumerating the pixels between the point M and the point I of the image plane Pl2 and by applying a rule of three. Moreover, the angle $\gamma = \arctan[MV/MI]$ is calculated so as to obtain the distance $AO = AI [\sin \beta/\sin(\alpha + \gamma)]$.

The distance sought CO is thus determined by subtracting the distance AO from the known distance AC which extends between the two edges, upper and lower, of the frame 10.

It will be observed that the angle α between the image plane Pl2 and the recess mid-plane PL2, can be obtained in a known manner by means of the calibrated rig 26, by triangulation, by virtue of a third tag situated at the center of the bridge 28 and which extends proud of the bridge.

Moreover, still in this near vision posture such as represented in FIG. 5, the length which extends between the corneal reflections of the two pupils 46, 48 is also measured, by enumerating the pixels which extend between the two reflections projected in the image plane Pl2 and by applying a rule of three as indicated hereinabove to determine the real distance.

Thereafter, the distance which extends between the points of intersection J for the far vision posture and O for the near vision posture is evaluated, by subtracting the value CO obtained by the near vision posture from the value CJ obtained by the far vision posture.

Finally, it is then possible to select progressive ophthalmic lenses whose progression length corresponds to said evaluated distance between the points of intersection O and J.

Figure 6:
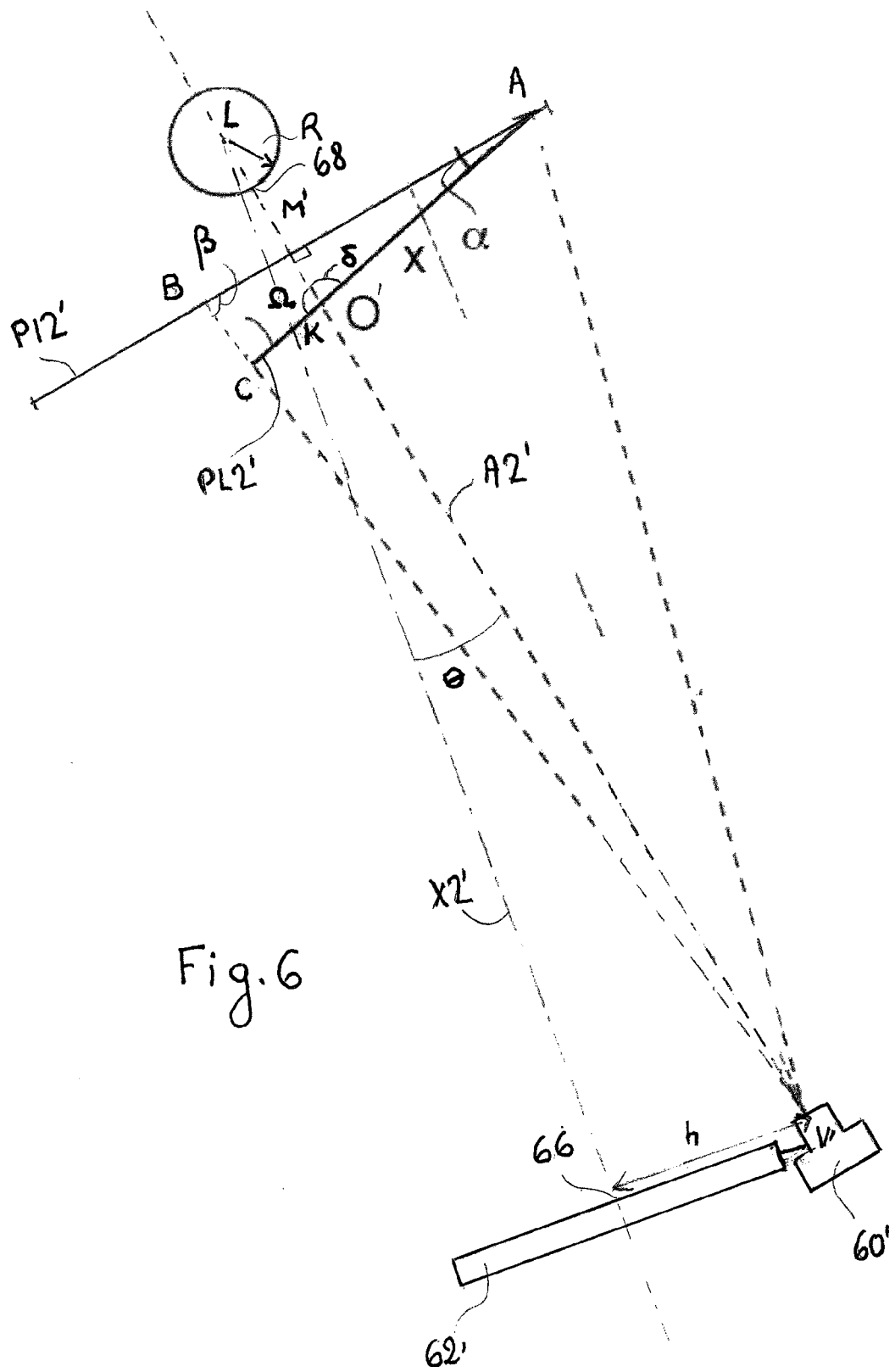
FIG. 6 is a schematic detail view according to another mode of implementation of the invention.

According to one particularly advantageous mode of implementation of the invention, illustrated in FIG. 6, where the elements and points strictly analogous to the previous illustrated in FIG. 5 exhibit the same references, while the analogous elements playing the same role are labeled with one and the same reference labeled with a prime sign "'", the support consists of a portable display screen 62', while the CCD digital camera 60' is installed securely on said portable display screen 62'. As will be explained hereinafter, the equipped portable display screen 62', exhibits a two-fold advantage. It makes it possible at one and the same time to orient the optical axis of the camera 60' toward the center of the eye L, thereby making it possible to improve the precision of the measurements, and also to constitute the near vision reading support for the wearer. However, a correction is necessary in order to take account of the position of the camera 60' with respect to the portable display screen 62', and in particular when the optical axis of the camera is inclined with respect to the display screen 62'.

Thus, with respect to FIG. 5, the relative position of the support 62 and now of the display screen 62' is rigorously identical. On the other hand, the digital camera 60' is no longer situated on the optical axis of the eye, but the optical axis of the camera 60' does cut the eye substantially at its center L. Furthermore, the second direction of gaze X2' is oriented toward a horizontal median 66 of the display screen 62', that it cuts substantially perpendicularly. This horizontal median 66 is here perpendicular to the plane of the figure.

Before describing the geometric consequences of this arrangement and determining the main useful parameters thereof, the operative conditions which enable same to be achieved will be explained.

Firstly, just as for the support 62 of the previous mode of implementation, the portable display screen 62' is grasped on each side by the wearer, who holds it at his near reading distance. This distance between the center of the eye L and the screen is around 40 cm. Hence, the orientation of the camera 60' with respect to the portable display screen 62' is preadjusted in such a way that the optical axis A2' of the camera 60' crosses the normal to the screen 62' cutting the center of the aforementioned median, and here coinciding with the second direction of gaze X2' at about 40 cm from the screen 62'.

Thereafter, the image obtained by virtue of the camera 60', corresponding to the image plane Pl2' is retransmitted on the portable display screen 62' in real time. Furthermore, the horizontal median line 66 which separates the screen into two equal parts, top and bottom, is displayed on the portable display screen 62'.

Thus, the wearer fitted with the frame furnished with the calibrated rig 26 is requested not only to adjust the portable display screen 62' in his normal position of near reading, but also to orient it in such a way that his eyes are centered laterally and that the median line cuts them at the level of the corneal reflection 68. Once in this position, the image is recorded. Indeed, in this position the optical axis A2' of the camera 60' cuts the center of the eye L. FIG. 6 thus schematically illustrates the situation side-on.

It will be observed that the optical axis A2' cuts the recess mid-plane PL2' at a second point O', while the second point of intersection of the second direction of gaze X2' cuts the recess mid-plane PL2' at a point K.

Here it is quite obviously the value of the distance CK that should be sought.

The value of the distance AO' is firstly easily determined since the angle α between the image plane Pl2' and the recess mid-plane PL2' in the triangle ABC is already known and the distance AM' in the image plane Pl2' is determined by calculating the number of pixels and applying a rule of three. The optical axis A2' cutting by definition the image plane Pl2' in a perpendicular manner, the distance AO' is therefore equivalent to $AM/\cos \alpha$.

It is now appropriate to determine the distance which separates the point O' from the point K.

Firstly, the distance which separates the point V' of the camera 60' at the point O' of the recess plane PL2' is ascertained by evaluating the number of pixels on the calibrated rig 26 and by operating a rule of three. Moreover, the distance which separates along this direction of the optical axis A2', the recess plane PL2' from the cornea of the eye at the level of the corneal reflection 68 has already been calculated, and it equals about 1.3 cm. And the mean radius R of an eye is known, about 0.8 cm, i.e. also the total distance LO'. Hence, the distance from the center of the eye L to the optical center V' of the camera 60' is deduced therefrom quite naturally. Moreover the distance h which separates the camera 60' from the horizontal median line 66 is known. Consequently, the center of the eye L, the optical center of the camera 60' and the point of intersection of the second direction of gaze X2' with the median line 66 forming a right-angled triangle, the value of the angle $\theta$ between the second direction of gaze X2' and the optical axis A2', and more precisely $\sin \theta$, is known and equals h/LV'.

Now, at the level of the triangle L, O', K, recognizes the distance LO', and the $\sin \theta$ of the angle between the segments LK and LO'. We must then determine the angle $\Omega$ between the segments LO' and O'K in order to be able to evaluate the segment O'K.

The angle $\Omega$, is equivalent to the difference between $\pi$ and the angle $\delta$ between the segment O'A and the segment O'M'. Now, the angle $\delta$ equals $\pi/2-\alpha$, and consequently the angle $\Omega$ equals $\alpha+\pi/2$.

Hence, knowing the length of a side of a triangle common to its two of its angles, from this is deduced the length of another side. And in this instance, O'K is equal to the ratio of the product O'L·$\sin \theta$ and of $\sin (\theta+\alpha+\pi/2)$. All these values being known, the value O'K is deduced therefrom quite naturally, and so the value of the segment AK, and more interestingly the value of CK, between the lower edge B of the frame and the center of the near vision K on the frame.

It will be observed that the calculation of the distance O'K is substantially different when the camera 62' is oriented in such a way that its optical axis A2' is perpendicular to the portable display screen 62', since in this case, the camera is parallel to the image plane Pl2'. Hence it is no longer the sine of the angle $\theta$ which is determined but its tangent h/V'L.

What is claimed is:

1. A method for selecting progressive ophthalmic lenses for a given frame and a given wearer, wherein said progressive ophthalmic lenses exhibit a far vision zone and a near vision zone spaced apart by a progression length;
    said given frame exhibiting two recesses configured respectively to receive a progressive ophthalmic lens, said two recesses defining a recess mid-plane;
    said frame is equipped with a calibrated rig exhibiting three tag points spaced apart respectively by a determined distance;
    said method comprising the following steps:
    a) said given wearer is fitted with said given frame;
    b) determining a position with respect to said frame of a first point of intersection of a first direction of gaze of said wearer in a far vision posture with said recess mid-plane;
    c) determining a position with respect to said frame of a second point of intersection of a second direction of gaze of said wearer in a near vision posture with said recess mid-plane;
    d) recording a second image of said frame equipped with said calibrated rig and the pupils of the eyes of said wearer along a direction neighboring said second direction of gaze, for determining said position of said second point of intersection with respect to said frame;
    e) evaluating a distance which extends between said points of intersection;
    f) providing progressive ophthalmic lenses whose progression length corresponds to said evaluated distance between said points of intersection; and
    g) providing a mobile support bearing inscriptions and a second camera secured to said mobile support and installed through said inscriptions, permitting said wearer fitted with said frame equipped with said calibrated rig to adjust said mobile support to a natural reading distance, so as to record said second image.

2. The method for selecting as claimed in claim 1, wherein in step b), a first image of said frame equipped with said calibrated rig and the pupils of the eyes of said wearer is recorded along a direction neighboring said first direction of gaze, so as to determine the position of said first point of intersection with respect to said frame.

3. The method for selecting as claimed in claim 2, wherein a first camera is provided and in that said first camera is adjusted remotely from said wearer fitted with said frame equipped with said calibrated rig and along a direction neighboring said first direction of gaze so as to record said first image.

4. An automatic processing assembly configured for enabling selection of progressive ophthalmic lenses for a given frame fitted on given wearer, wherein the progressive ophthalmic lenses exhibit a far vision zone and a near vision zone spaced apart by a progression length, and wherein said given frame exhibits two recesses able respectively to receive a progressive ophthalmic lens, said two recesses defining a recess mid-plane;
    said assembly comprises:
        first determination means for determining with respect to said frame, the position of a first point of intersection of a first direction of gaze of said wearer in a far vision posture with said recess mid-plane;
        second determination means for determining with respect to said frame, the position of a second point of intersection of a second direction of gaze of said wearer in a near vision posture with said recess mid-plane;
        evaluation means for evaluating the distance which extends between said points of intersection;
        selection means configured for selecting progressive ophthalmic lenses whose progression length corresponds to said evaluated distance between said points of intersection;
    wherein said first and second determination means comprise a calibrated rig configured and operable to equip said frame, and said rig exhibiting three tag points spaced apart respectively by a determined distance;
    a first camera which is adjustable remotely from said wearer fitted with said frame equipped with said calibrated rig and along a direction neighboring said first direction of gaze so as to record said first image;
    said second determination means comprise a portable display screen and a second camera installed on said portable display screen; and
    said second determination means further comprise recording and calculation means, for recording the images provided by said second camera and for calculating said position of the second point of intersection of the second direction of gaze of said wearer in a near vision posture with said recess mid-plane; and
    a mobile support bearing inscriptions and the second camera secured to said mobile support and installed through said inscriptions said mobile support is adjustable to a selected distance and said camera is operable to record said second image.

* * * * *